(12) United States Patent
Hart

(10) Patent No.: US 7,454,969 B2
(45) Date of Patent: Nov. 25, 2008

(54) FUEL DENSITY MEASURING DEVICE, SYSTEM, AND METHOD USING MAGNETOSTRICTIVE PROBE BOUYANCY

(75) Inventor: Robert P. Hart, East Hampton, CT (US)

(73) Assignee: Veeder-Root Company, Simsbury, CT (US)

( * ) Notice: Subject to any disclaimer, the term of this patent is extended or adjusted under 35 U.S.C. 154(b) by 215 days.

(21) Appl. No.: 11/141,282

(22) Filed: May 31, 2005

(65) Prior Publication Data

US 2006/0266113 A1    Nov. 30, 2006

(51) Int. Cl.
*G01F 23/56* (2006.01)
*G01N 9/18* (2006.01)

(52) U.S. Cl. .................. 73/306; 73/290 R; 73/313; 73/447; 702/25

(58) Field of Classification Search ............ 73/306, 73/290 R, 313, 447; 702/25
See application file for complete search history.

(56) References Cited

U.S. PATENT DOCUMENTS

| | | | | |
|---|---|---|---|---|
| 2,620,661 | A | 12/1952 | Roux | 73/313 |
| 2,911,828 | A | 11/1959 | Keating et al. | 73/290 R |
| 4,155,254 | A | 5/1979 | Colditz | 73/447 |
| 4,193,303 | A | 3/1980 | Egnell | |
| 4,625,553 | A | 12/1986 | Charter | |
| 4,924,700 | A | 5/1990 | Habart | 73/290 V |
| 4,943,773 | A | 7/1990 | Koski et al. | 324/207.13 |
| 4,952,873 | A | 8/1990 | Tellerman | 324/207.13 |
| 4,977,528 | A | 12/1990 | Norris | |
| 5,017,867 | A | 5/1991 | Dumais et al. | 324/207.13 |
| 5,050,430 | A | 9/1991 | Begin et al. | 73/313 |
| 5,076,100 | A | 12/1991 | Hunter et al. | 73/290 V |
| 5,136,884 | A | 8/1992 | Lovett | 73/313 |
| 5,193,912 | A * | 3/1993 | Saunders | 374/179 |
| 5,319,545 | A | 6/1994 | McGarvey et al. | 705/28 |
| 5,400,253 | A | 3/1995 | O'Connor | 701/123 |
| 5,412,316 | A | 5/1995 | Dumais et al. | 324/207.13 |
| 5,423,457 | A | 6/1995 | Nicholas et al. | 222/62 |
| 5,471,873 | A | 12/1995 | Nyce et al. | 73/453 |
| 5,473,245 | A | 12/1995 | Silvus, Jr. et al. | 324/207 |
| 5,640,880 | A | 6/1997 | Mulrooney et al. | 73/313 |

(Continued)

FOREIGN PATENT DOCUMENTS

WO    WO 2004013583 A1 *    2/2004

OTHER PUBLICATIONS

Veeder-Root, "Mag 1 & 2 Plus! Probes Assembly Guide" Manual No. 577013-744, Revision C, 2003, 10 pages.

(Continued)

*Primary Examiner*—Thomas P Noland
(74) *Attorney, Agent, or Firm*—Nelson Mullins Riley & Scarborough LLP

(57) ABSTRACT

A magnetostrictive fuel level probe includes a spring-loaded foot. The probe shaft of the fuel level probe moves up and down within the spring-loaded foot as a function of fuel density. The spring-loaded foot includes a reference magnet whose height relative to the bottom of a fuel storage tank is fixed. Currents generated by the fuel level probe allow measurement of how much of the fuel level probe is positioned above the reference magnet, and from this measurement, the buoyancy of the fuel level probe may be measured. From the buoyancy of the fuel level probe, the fuel density may be calculated.

26 Claims, 6 Drawing Sheets

U.S. PATENT DOCUMENTS

| | | | |
|---|---|---|---|
| 5,734,851 A | 3/1998 | Leatherman et al. | 715/771 |
| 5,814,830 A | 9/1998 | Crowne | 250/577 |
| 5,848,549 A | 12/1998 | Nyce et al. | 73/319 |
| 5,956,259 A | 9/1999 | Hartsell, Jr. et al. | |
| 6,052,629 A | 4/2000 | Leatherman et al. | 700/241 |
| 7,278,311 B1 | 10/2007 | Demin | 73/313 |
| 2004/0093942 A1 | 5/2004 | Brun | 73/301 |
| 2006/0048569 A1* | 3/2006 | Manfiotto et al. | 73/304 R |
| 2006/0169039 A1 | 8/2006 | Zalenski et al. | 73/290 |
| 2006/0248952 A1 | 11/2006 | Jarvie | 73/444 |
| 2007/0295085 A1 | 12/2007 | Demin | 73/447 |

OTHER PUBLICATIONS

Setra, "Model 201 Pressure Transducer; Very Low Differential Gauge Pressure", from http://www.setra.com, 5 pages, Nov. 2000.

Veeder-Root, "Mag Inventory Measurement Probe", from http://www.veeder.com/dynamic/index.cfm?PageID=103, 2 pages, by May 2005.

Veeder-Root, "Mag Plus Inventory Measurement Probe", from http://www.veeder.com/dynamic/index.cfm?PageID=274, 2 pages, by May 2005.

MTS Systems Corp. USA, "How They Work, Magnetostrictive Linear Position Sensors", from http://www.sensorland.com/HowPage024.html, 3 pages, by May 2005.

Brochure entitled "Best-In-Class Tank Gauge Innovation," OPW Fuel Management Systems, Oct. 2007.

Co-pending U.S. Appl. No. 11/838,281 filed Aug. 14, 2007, issuing Jul. 22, 2008 as U.S. Pat. No. 7,403,860.

* cited by examiner

FUEL DENSITY MEASURING DEVICE, SYSTEM, AND METHOD USING MAGNETOSTRICTIVE PROBE BOUYANCY

FIELD OF THE INVENTION

The present invention relates to a probe device, system, and method used in a fuel storage tank that can be used to determine the density of the fuel stored within the fuel storage tank.

BACKGROUND OF THE INVENTION

Fueling environments typically store fuel in large storage tanks located beneath the ground, sometimes referred to as "underground storage tanks" (UST). To comply with environmental laws, rules, and regulations, these storage tanks may be double-walled and equipped with various leak detection sensors and inventory reconciliation systems. One popular leak detection sensor is sold by Veeder-Root Company of 125 Powder Forest Drive, Simsbury, Conn. 06070, the assignee of the present application, under the name "The MAG Plus Inventory Measurement Probe" (Mag Probe). This probe is typically matched with a tank monitor, such as the TLS-350R, also sold by Veeder-Root Company. Such probes measure a height of fuel within the storage tank and may optionally measure a height of water (if present). The measurements are reported to the tank monitor for usage by the operator of the fueling environment to evaluate and reconcile fuel inventory and/or detect leaks, as is well understood.

While the United States has many rules and regulations relating to leak monitoring within fueling environments, other locales have additional requirements for fueling environments. For example, countries such as India and Russia have seen a rise in fraud at fueling environments, and have consequently taken steps to combat such fraud. Specifically, these countries have become aware that dilution of the fuel within storage tanks may be used as a technique to defraud a customer. One way in which the diluted fuel is created is through the addition of alcohol to the fuel storage tank. The alcohol allows the water at the bottom of the fueling tank to mix with the fuel, and the diluted mixture is then dispensed as normal through the fuel dispensers.

To combat this fraud, some governments have mandated that fuel density be measured. If the density is outside of a predetermined allowable range, it may be inferred that the fuel has been adulterated. Even if some countries or governments do not have such legislation requiring measurement of density of fuel, some fuel distribution companies that operate service stations may nonetheless find it desirable to monitor the density of their fuel for quality control purposes.

Density measurements also assist in calculation of the mass of fluid within a storage container. Differences in mass may be used to perform leak detection for fluids in situations where normal volume detection techniques are inadequate (e.g., waste oil storage containers). These situations create additional demand for density measuring devices.

All the devices currently known to be available commercially that are capable of measuring fuel density in a conventional fueling environment fuel storage tank are stand alone peripherals, requiring their own power and interface connections. Furthermore, these devices tend to have a limited range of values over which fuel density can be measured. Such stand alone peripherals are not desirable as a result of these deficiencies.

An additional concern that arises in the measurement of fuel density is that the density of the fuel is not typically uniform at all fuel levels in an underground storage tank. For example, there may be thermal stratification which results in non-uniform densities at particular levels within the fuel storage tank. Likewise, surface thermal effects can be large. That is, when the surface of the fuel is much warmer than the bulk of the stored fuel, the density of the surface fuel relative to the bulk of the fuel is reduced. If the density of the fuel is measured just at the surface, the measurement will not accurately reflect the density of the bulk of the fuel. Any density measuring device should be able to address these issues.

In response to these concerns, the Assignee of the present invention presented the fuel density measurement system of commonly-owned U.S. patent application Ser. No. 11/048, 145, filed Feb. 1, 2005. While the '145 Application provides one solution to the concerns raised above, there remains a need for a simpler solution.

SUMMARY OF THE INVENTION

The present invention is an improvement on a conventional fuel level probe that measures the height of fuel in a fuel storage tank. Specifically, the present invention is a magnetostrictive probe which has a probe shaft with a moveable foot on the terminal end of the probe shaft. The foot has a reference magnet whose position relative to the bottom of the fuel storage tank is fixed. The foot also includes an internal spring that allows the probe to move up and down within the foot as a function of the buoyancy of the probe shaft. The buoyancy of the probe shaft is a function of the height of the fuel that buoys the probe and the density of the fuel in which the probe shaft is placed. Other directly measurable or calculable variables may also contribute to the buoyancy of the probe shaft, and the algorithms of the present invention compensate for these other variables in the calculation of the fuel density. Based on the position of the probe shaft relative to the reference magnet, the height of the fuel, the spring constant of the internal spring, and other measurable or known variables, the density of the fuel may be derived and used as needed.

In operation, the present invention sends a current down a magnetostrictive wire within the probe shaft. The current in the magnetostrictive wire interacts with the reference magnet and introduces a torsional wave in the wire which is detected by the probe. The time elapsed between the signal generation and the arrival of the torsional wave may be used to measure the distance from the probe to the magnet. As the probe moves up and down within the foot as a function of the buoyancy, the distance measured will change and thus, the probe can measure the buoyancy of the probe shaft. In effect, the density of the fuel may be derived from the measured buoyancy of the probe shaft. The probe may either perform the calculations to arrive at the density of the fuel or may report its measurements to a tank monitor or other controller so that the controller may perform the calculations to determine the density of the fuel.

In one structural embodiment, the probe includes a probe canister attached to a probe shaft. The probe shaft has a terminal end and is designed to be inserted into the fuel storage tank. A foot is secured to the terminal end of the probe shaft. The foot includes an inner cup that fits over the probe shaft and an outer cup that the inner cup and probe shaft fit within. The reference magnet is secured fixedly to the outer cup. A spring is positioned between the two cups. Initially, the outer cup rests on the bottom of the fuel storage tank, and the full weight of the probe compresses the spring between the cups.

As fuel is introduced into the fuel storage tank, the fuel causes the probe to "float," thereby reducing the compression of the spring. Thus, the probe shaft moves up and down within the outer cup. The force exerted upwardly by the spring is equal to the weight of the probe minus the buoyancy of the probe. Because the reference magnet is fixed and the probe shaft floats relative to the reference magnet, it is possible to determine how much of the probe shaft is positioned above the reference magnet. That is, when a current is generated in the magnetostrictive wire within the probe shaft, the time elapsed between current generation and the arrival of the torsional wave generated by the reference magnet will allow calculation of the amount of the probe shaft above the reference magnet. The amount of the probe shaft above the reference magnet is then used in another calculation, along with the spring constant and the volume of the probe shaft, to arrive at the density of the fuel.

Those skilled in the art will appreciate the scope of the present invention and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the invention, and together with the description serve to explain the principles of the invention.

DETAILED DESCRIPTION OF THE PREFERRED EMBODIMENTS

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

The present invention is a fuel level probe that measures fuel density as well as fuel height in a fuel storage tank. An exemplary fuel level probe is a magnetostrictive probe which has a probe shaft with a moveable foot on the terminal end of the probe shaft. The foot has a reference magnet whose position relative to the bottom of the fuel storage tank is fixed. The foot also includes an internal spring that allows the probe to move up and down within the foot as a function of the buoyancy of the probe shaft. The buoyancy of the probe shaft is a function of the density of the fuel in which the probe shaft is placed. Other directly measurable or calculable variables, such as the fuel height, may also contribute to the buoyancy of the probe shaft, and the algorithms of the present invention compensate for these variables in the calculation of the fuel density. In operation, the present invention sends a current down a magnetostrictive wire within the probe shaft. The current in the magnetostrictive wire interacts with the reference magnet and introduces a torsional wave in the wire which is detected by a sensor in the probe. The time elapsed between the signal generation and the arrival of the torsional wave may be used to measure the distance from the sensor to the magnet. As the probe moves up and down within the foot as a function of the buoyancy, the distance measured will change and thus, the probe can measure the buoyancy of the probe shaft. The density of the fuel is then derived from this measurement. The probe may either perform the calculations to arrive at the density of the fuel or may report its measurements to a tank monitor or other controller so that the controller may perform the calculations to determine the density of the fuel. The density of other fluids may also be measured with the probe of the present invention and the invention is not strictly limited to use in a fueling environment.

Figure 1:
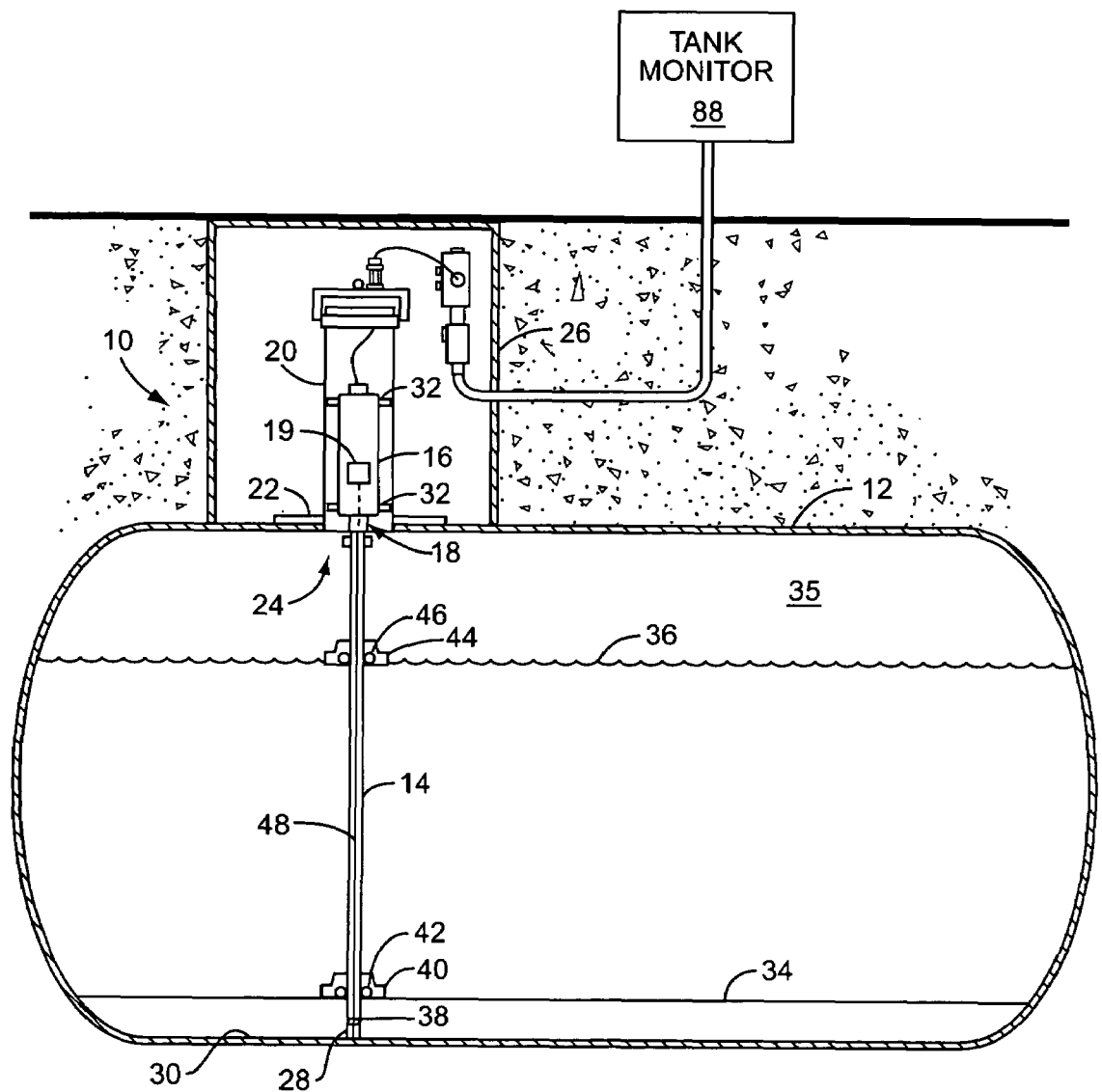
FIG. 1 illustrates a conventional magnetostrictive probe positioned in a fuel storage tank.

Because the present invention relates closely to a magnetostrictive fuel level probe, a discussion of a conventional magnetostrictive fuel level probe 10 (hereinafter "probe") is first presented herein with reference to FIG. 1, and the discussion of the present invention follows beginning with reference to FIG. 2 below.

The probe 10 is a magnetostrictive probe, such as the MAG PROBE™ magnetostrictive probe sold by the assignee of the present invention, namely Veeder-Root Company of 125 Powder Forest Drive, Simsbury, Conn. 06070 (see, for example, http://www.veeder.com/dynamic/index.cfm?PageID=103 and http://www.veeder.com/dynamic/index.cfm?PageID=274).

The probe 10 is positioned partially in a fuel storage tank 12. Specifically, the probe includes a probe shaft 14 that extends into the fuel storage tank 12 while a canister 16 is positioned outside of the fuel storage tank 12. The canister 16 is attached to the probe shaft 14 via fittings 18. The canister 16 includes electronics 19, which enable operation of the probe 10 as further explained below.

During installation, the probe 10 is lowered into the fuel storage tank 12 through a riser pipe 20 that is secured to the fuel storage tank 12 with a flange 22. The riser pipe 20 is typically a four inch (10.16 cm) pipe. The fuel storage tank 12 has an aperture 24 therein that fluidly couples the interior of the riser pipe 20 with the interior of the fuel storage tank 12 and through which the probe shaft 14 extends. The riser pipe 20 may be positioned within a sump 26 (illustrated) or not (not illustrated) as needed or desired. The probe shaft 14 goes through the aperture 24 and a terminal end 28 of the probe shaft rests on the bottom 30 of the fuel storage tank 12. The weight of the probe 10 keeps the terminal end 28 on the bottom 30. The canister 16 is not secured to the riser pipe 20, but may be spaced from the sides of the riser pipe 20 by one or two spacers 32. It should be appreciated that the spacer(s) 32 may restrict horizontal movement of the canister 16, but does not materially restrict vertical movement of the canister 16.

In use, most fuel storage tanks, such as fuel storage tank 12, have a small amount of water therein. This water collects at the bottom of the fuel storage tank 12, forming a water-fuel interface 34. The fuel sits on top of the water and has an air-fuel interface 36 at the ullage 35 of the fuel storage tank 12. The probe shaft 14 extends through both interfaces 34 and 36. The probe shaft 14 has a reference magnet 38 positioned proximate a terminal end 28 of the probe shaft 14 at a fixed, known distance from the terminal end 28. The reference magnet 38 may be positioned internal to the probe shaft 14 as is conventional, or externally in a boot (not shown) that slips over the end of the probe shaft 14. A water level float 40, typically an annular float, is positioned on the probe shaft 14 and floats at the level of the water-fuel interface 34. A water level magnet 42 is associated with the water level float 40 so that the level of the water in the fuel storage tank 12 can be ascertained.

A fuel level float 44, also generally an annular float, is positioned on the probe shaft 14 and floats at the air-fuel interface 36. A fuel level magnet 46 is associated with the fuel level float 44 so that the level of the fuel in the fuel storage tank 12 can be ascertained. It should be appreciated that the floats 40 and 44 move freely up and down the probe shaft 14 as the respective levels of fluids (water and fuel) change. Likewise, the buoyancy of the floats 40 and 44 is determined by the fluid on which they will be floating. Such parameters are conventional and well understood by someone of ordinary skill in the art. However, the interested reader is directed to the MAG 1 & 2 PLUS! PROBES ASSEMBLY GUIDE, published by Veeder-Root, which is available online at http://vrnotesweb1.veeder.com/vrdocrep.nsf/Files/577013-764/$File/577013-744.pdf, and is submitted as part of an Information Disclosure Submission accompanying this application at the time of filing. The ASSEMBLY GUIDE is hereby incorporated by reference in its entirety.

To determine the fuel level and the water level within the fuel storage tank 12, the probe 10 generates an electric current with a current source within the electronics 19 positioned in the canister 16 and sends the electric current down a magnetostrictive wire 48 in the probe shaft 14. Then, the probe 10 detects torsional wave reflections induced by the magnets 42 and 46 of the floats 40 and 44 respectively and the reference magnet 38. The torsional wave reflections are detected with a detector such as a sensing coil (not shown explicitly) of the electronics 19. The first reflection to arrive at the detector is a reflection from the fuel level magnet 46 associated with the fuel level float 44. The second reflection to arrive at the detector is a reflection from the water level magnet 42 associated with the water level float 40. A third reflection arrives from the reference magnet 38. Since the speed of the torsional wave in the magnetostrictive wire 48 is known (typically about 3000 m/s), it is possible to calculate the distance between the detector and the magnet that induced the torsional wave. The detector thus measures the time elapsed between the origination of the pulse and the arrival of each torsional wave reflection. If the distance from the detector to a particular magnet is known, it is a well known exercise to determine the level of that particular magnet within the fuel storage tank 12. Alternatively, the difference in arrival times of torsional waves is used to measure the distance between the level magnets and the reference magnet 38. That is, the distance from the bottom 30 to the reference magnet 38 (the height of the reference magnet) is known (typically about one-half inch (~1.25 cm)) at the time of manufacturing. By measuring the time difference between arrival of torsional waves from, for example, the water level magnet 42 and the reference magnet 38, the distance between the two magnets 38 and 42 may be determined. Specifically, the velocity of the torsional wave is multiplied by the time, and a distance is generated. This distance is added to the height of the reference magnet and from this calculation, the height of the water level magnet 42 is determined. Similar calculations may be made for the fuel level magnet 46. Put another way, the heights of the magnets relative to the bottom of the fuel storage tank 12 are determinable.

The probe 10 reports the measured reflections to a tank monitor 88, such as the TLS-350R manufactured and sold by Veeder-Root Company. The tank monitor 88 uses the data from the probe 10, and specifically, the measured reflections to determine the level and thus, the volume of fuel, within the fuel storage tank 12. For example, the tank monitor 88 may determine a volume of fuel within the fuel storage tank from the height of the fuel level, as determined by the height of the fuel level float 44 (and as measured by the first reflection or it's relationship to the reference magnet's 38 reflection). From this height, a conventional tank strapping algorithm or other conventional technique may be applied, as is well understood in the art, to convert the fuel level to arrive at the volume of fuel within the fuel storage tank 12. For more information on the operation of a magnetostrictive fuel level probe, the interested reader is referred to U.S. Pat. No. 5,076,100, which is hereby incorporated by reference in its entirety.

Figure 2:
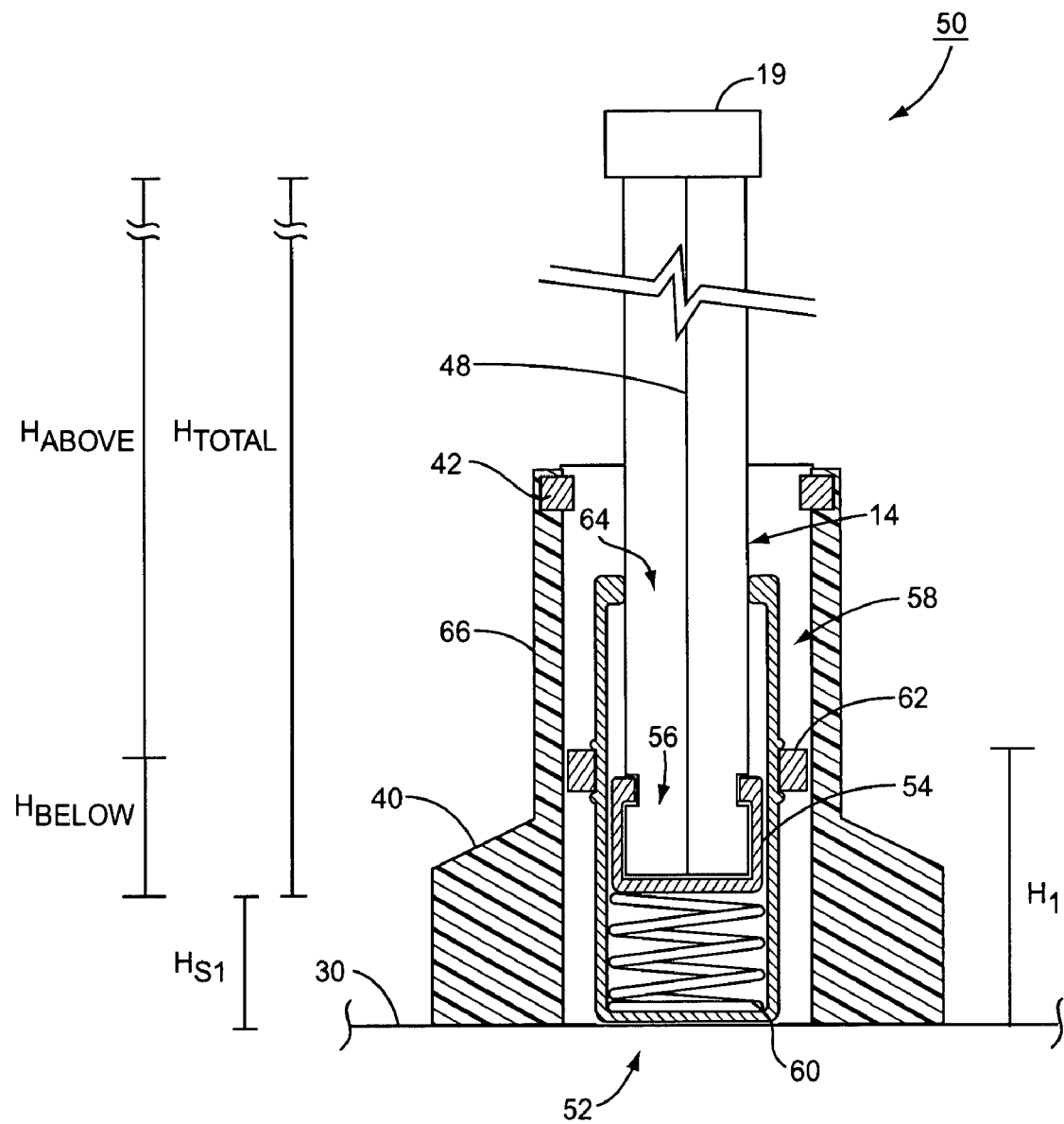
FIG. 2 illustrates a probe according to a first embodiment of the present invention.

The modified probe 50 (hereinafter "probe"), in accordance with one embodiment of the present invention, is illustrated in FIG. 2. In general, the probe 50 has components that are substantially similar to the components of the probe 10. As such, where the component is identical to the component of probe 10, the same number is used. FIG. 2 illustrates, a modified foot 52 of the probe 50. The modified foot 52 includes an inner cup 54 that may, in an exemplary embodiment, snap fit over a terminal end 56 of the probe shaft 14. An outer cup 58 fits over the inner cup 54 and sandwiches a spring 60 between the inner cup 54 and the outer cup 58. In particular, the spring 60 is positioned between an outer bottom surface of the inner cup 54 and an inner floor surface of the outer cup 58.

The outer cup 58 also has a reference magnet 62 fixedly attached to an outer surface of the outer cup 58. In an exemplary embodiment, the reference magnet 62 is an annulus and fits around the circumference of the outer cup 58. Other arrangements are possible. For example, the reference magnet 62 could be positioned inside the outer cup 58 and does not have to be an annulus. Such permutations on the position and shape of the reference magnet 62 are within the scope of the present invention. A lower portion 64 of the probe shaft 14 is positioned within the outer cup 58 and moves up and down within the outer cup 58 as will be explained in greater detail below.

The water level float 40 fits over the modified foot 52 and the probe shaft 14, and may include an extended neck 66. The extended neck 66 spaces the water level magnet 42 from the reference magnet 62 so that torsional waves introduced by the magnets 42 and 62 may be differentiated by the detector within canister 16. Empirical evidence indicates that approximately one inch (2.54 cm) should exist between the two magnets 42 and 62 for discrimination therebetween. It should be appreciated that the size of the modified foot 52 is designed such that the modified foot 52 does not interfere with the movement of the water level float 40.

As is illustrated in FIG. 2, an outer bottom surface of the outer cup 58 rests on the bottom 30 of the fuel storage tank 12. The weight of the probe 50 keeps the outer cup 58 firmly positioned on the bottom 30. Thus, the position of the reference magnet 62 relative to the bottom 30 of the fuel storage tank 12 is fixed. Even if some geologic force or other event changes the shape of the fuel storage tank 12, the distance between the reference magnet 62 and the bottom 30 will be $H_1$, as illustrated in FIG. 2.

FIG. 2 illustrates the probe 50 when it is first inserted into an empty fuel storage tank 12. That is, there is no fluid within fuel storage tank 12. As a result, the full weight ($W_p$) of the probe 50 is positioned above the spring 60 and compresses the spring 60. Under normal operating conditions, the weight of the probe 50 is constant. The spring 60 has a spring constant $K_s$. $K_s$ is chosen such that the spring 60 is not fully compressed when the full weight $W_p$ of the probe 50 acts on the spring 60. However, the weight of the probe 50 will compress the spring 60 away from its initial height $H_{s0}$ to some reduced height $H_{s1}$. $H_{s0}$ is known and $H_1$ can be calculated or measured as needed or desired.

To calculate $H_{s1}$, and thus ultimately determine the amount of the probe shaft 14 above the reference magnet 62, the present invention first subtracts the amount of magnetostrictive wire 48 above ($H_{ABOVE}$) the reference magnet 62 from the known total length ($H_{TOTAL}$) of the magnetostrictive wire 48. $H_{TOTAL}$ is known a priori. Measuring the torsional wave induced in the magnetostrictive wire 48 by the reference magnet 62 provides an effective measurement of $H_{ABOVE}$. Subtracting $H_{ABOVE}$ from $H_{TOTAL}$ gives a measurement of the amount of magnetostrictive wire 48 below $H_{BELOW}$ the reference magnet 62. As the height of the reference magnet 62 is known, subtracting $H_{BELOW}$ from $H_1$ gives a good approximation of the height of the loaded spring 60 $H_{s1}$. Mathematically, this is formulated as follows:

$$H_{s1} = H_1 - H_{BELOW}, \text{ where } H_{BELOW} = H_{TOTAL} - H_{ABOVE}$$

or $$H_{s1} = H_1 - (H_{TOTAL} - H_{ABOVE})$$

Basic physics requires the weight of the probe 50 is equal to the amount of force that the spring 60 is exerting upwards against the probe 50. Applying Hook's Law, the equation can be presented as follows:

$$K_s(H_{s0} - H_{s1}) = W_p$$

This formula may be used to calibrate the probe 50 when it is initially installed if needed or desired, since all the values should be known before installation.

When fluid is introduced into the fuel storage tank 12, the fluid will exert a buoyant force on the probe 50, in effect bearing some of the weight of the probe 50 and lifting this weight off the spring 60. This buoyant force will allow the spring 60 to decompress from its compressed height of $H_{s1}$. This situation is shown in FIG. 3, with the water level float 40 removed for ease of comprehension.

Figure 3:
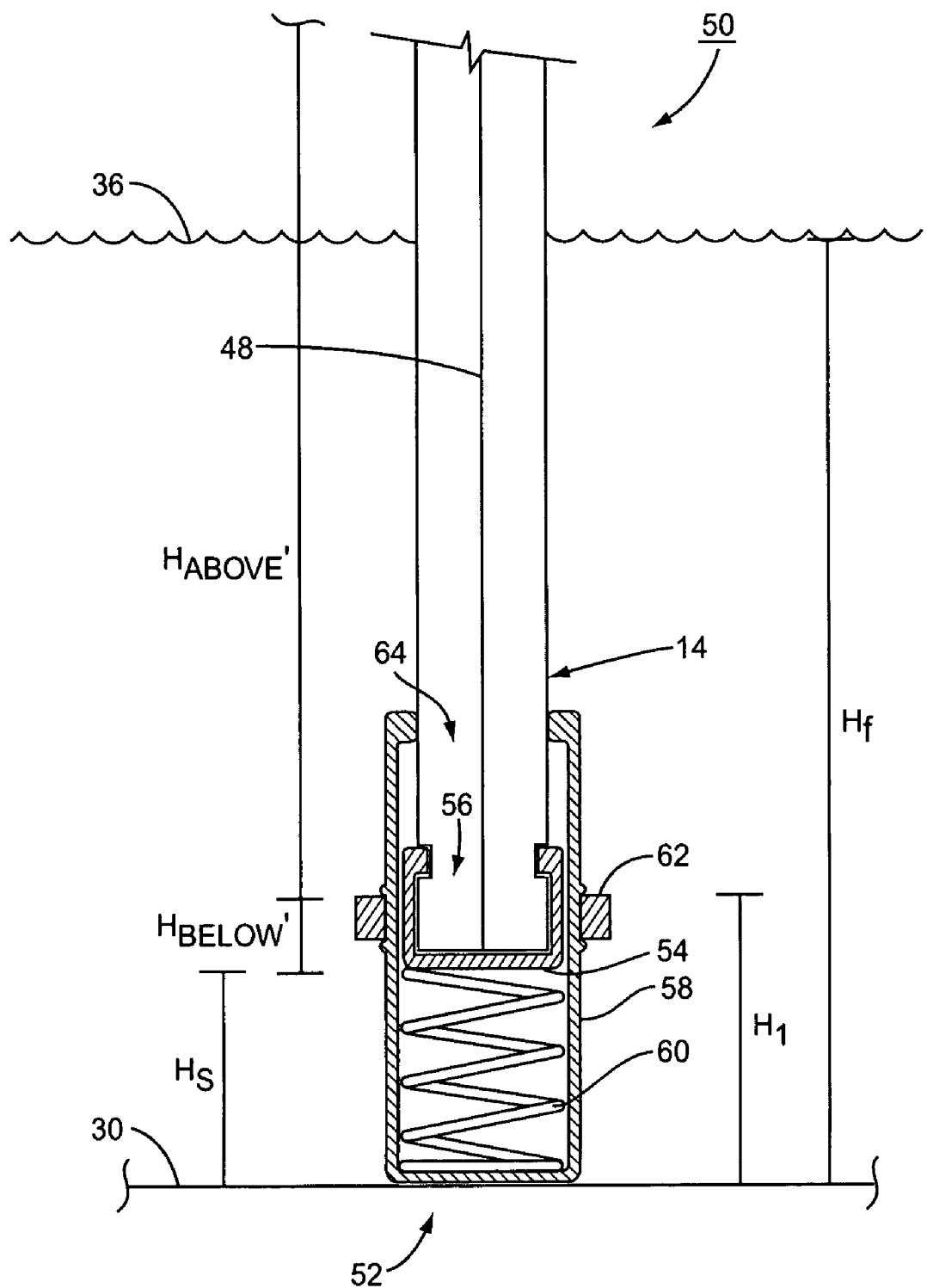
FIG. 3 illustrates the probe of FIG. 2 inserted into a fuel storage tank with fuel therein such that the probe is buoyed upwardly.

As is readily seen in FIG. 3, the fuel positioned within the fuel storage tank 12 is bearing some of the weight of the probe 50, causing the probe 50 to exert less force on the spring 60, which in turn allows the spring 60 to expand such that it is at some variable height $H_s$. It is to be understood that the probe 50 would not be so buoyant as to remove all weight from the spring 60. Thus, $H_s < H_{s0}$. The force of the spring 60 is now modeled by:

$$F_s = K_s(H_{s0} - H_s) = W_p - B_p, \text{ where } B_p \text{ is the buoyancy of the probe 50.}$$

The buoyancy of the probe 50 is a function of the volume of the probe 50 within the fuel and the density of the fluid within the fuel storage tank 12. The spring-loaded modified foot 52 allows the probe 50 to rise and fall relative to the modified foot 52, with the rising and falling being dependent on increasing and decreasing fuel density respectively and other variables. Each of the other variables is known or can be calculated. Based on this knowledge and these calculations, the density of the fuel ($D_f$) may be calculated. Stepwise, calculation of $D_f$ is as follows:

$$F_s = W_p - B_p$$

$B_p = D_f * V_p$, where $V_p$ is the volume of the probe 50 in the fuel.

The volume of the probe 50 within the fuel is readily calculated as the cross-sectional area of the probe 50 ($A_p$) multiplied by the height of the probe 50 within the fuel ($H_p$). Or, substituting into the equation above:

$$B_p = D_f * A_p * H_p$$

$H_p$ can be calculated from the height of the fuel ($H_f$) minus the height of the spring 60 ($H_s$). The calculation of $H_f$ is known from conventional fuel level probe technology. Substituting into the equation above:

$$B_p = D_f * A_p * (H_f - H_s)$$

If this equation is substituted back into the equation of the force of the spring 60, the result is as follows:

$$K_s(H_{s0} - H_s) = W_p - D_f A_p (H_f - H_s)$$

Solving for $D_f$, the equation becomes:

$$D_f = \frac{W_p - K_s(H_{s0} - H_s)}{A_p(H_f - H_s)}$$

Thus, the movement of the probe 50 may be used to measure the density of the fuel within the fuel storage tank 12. Likewise, this arrangement effectively measures the density of the fuel throughout the fuel storage tank 12. In this manner, errors that might be caused by thermal stratification are reduced or eliminated. Likewise, any density variations that may result from surface thermal effects are averaged away such the density measurement reflects the average of the entire volume of fuel rather than merely a single layer of fuel within the fuel storage tank 12.

Figure 5:
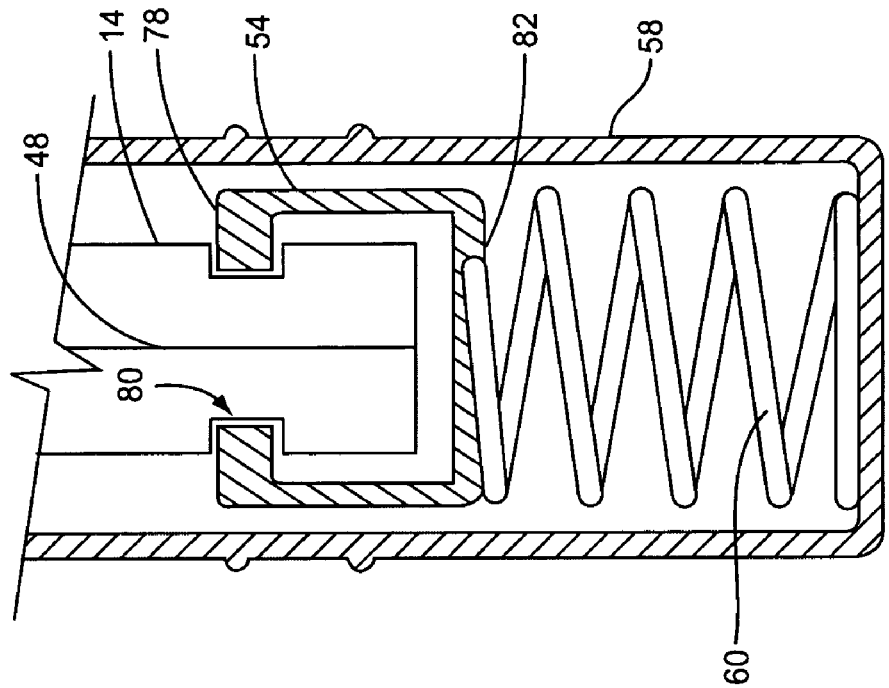
FIG. 5 illustrates a second embodiment of the cups of the foot of the probe where the spring is secured to the inner cup.
Figure 4:
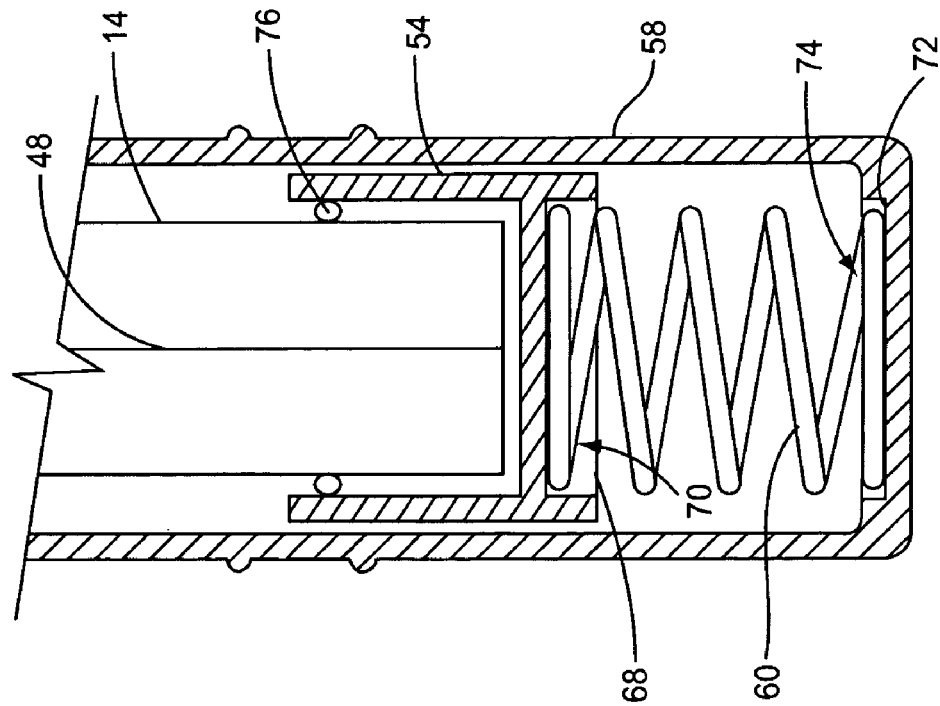
FIG. 4 illustrates a first embodiment of the cups of the foot of the probe.

While the embodiment of FIGS. 2 and 3 are fully functional, there are other variations of the present invention. For example, the placement of the spring 60 may be varied and/or the nature of the inner cup 54 attachment to the probe shaft 14 may be varied to accommodate differing engineering and/or design constraints. FIGS. 4 and 5 illustrate some of these variations.

In FIG. 4, a first variation in the placement of the spring 60 that helps inhibit lateral movement of the spring 60 is illustrated. Specifically, the inner cup 54 has an indentation 68 which is sized to receive a top end 70 of the spring 60. The indentation 68 helps hold the spring 60 in a fixed lateral position within the outer cup 58. The outer cup 58 may likewise have an indentation 72 that is sized to receive a bottom end 74 of the spring 60. Again, the indentation 72 helps hold the spring 60 in a fixed lateral position within the outer cup 58. By limiting the lateral movement of the spring 60, the likelihood that the spring 60 becomes misaligned is reduced, and the functionality of the present invention is preserved. While the indentations 68 and 72 help reduce the lateral movement of the spring 60, it is possible that the sizes of the inner cup 54 and the outer cup 58 are such that the lateral movement of the spring 60 is sufficiently constrained to stop misalignment of the spring 60. Thus, the indentations 68 and 72 are optional, and are not central to the present invention.

FIG. 4 also illustrates a variation on the means of attaching the inner cup 54 to the probe shaft 14. Specifically, the inner cup 54 may be held on the probe shaft 14 via an elastomeric o-ring 76. The space between the inner cup 54 and the probe shaft 14 is small and the diameter of the elastomeric o-ring 76 is slightly greater than the space between the inner cup 54, and the probe shaft 14. The elastomeric o-ring 76 may be positioned on the probe shaft 14 and the inner cup 54 slipped over the probe shaft 14, compressing the elastomeric o-ring 76 therebetween. The elastomeric o-ring 76 presses outwardly against both the probe shaft 14 and the inner cup 54 holding the inner cup 54 in a desired position relative to the probe shaft 14.

FIG. 5 illustrates alternate variations on the means of attaching. In place of the elastomeric o-ring 76, the inner cup 54 may include a flange 78 that is adapted to snap fit within a recess 80 on the end of the probe shaft 14. This variation more fixedly secures the inner cup 54 on the end of the probe shaft 14 than the o-ring embodiment, but may be more manufacturingly intense. Other mechanisms may be used to secure the inner cup 54 to the probe shaft 14 without departing from the scope of the present invention.

FIG. 5 also illustrates an alternate mechanism of the present invention to keep the spring 60 properly aligned. In this embodiment, the spring 60 is fixedly secured to the lower surface 82 of the inner cup 54. Spring 60 may be secured to the lower surface 82 by positioning the spring 60 when the inner cup 54 is molded. Alternatively, the spring 60 may be welded to the inner cup 54, or other technique as needed or desired, depending on the material used in the construction of the inner cup 54. In an exemplary embodiment, the spring 60 is a non-magnetic, stainless steel spring, although other materials may be used if needed or desired. All materials should be chosen to withstand extended submersion in a petroleum based fluid.

Figure 6:
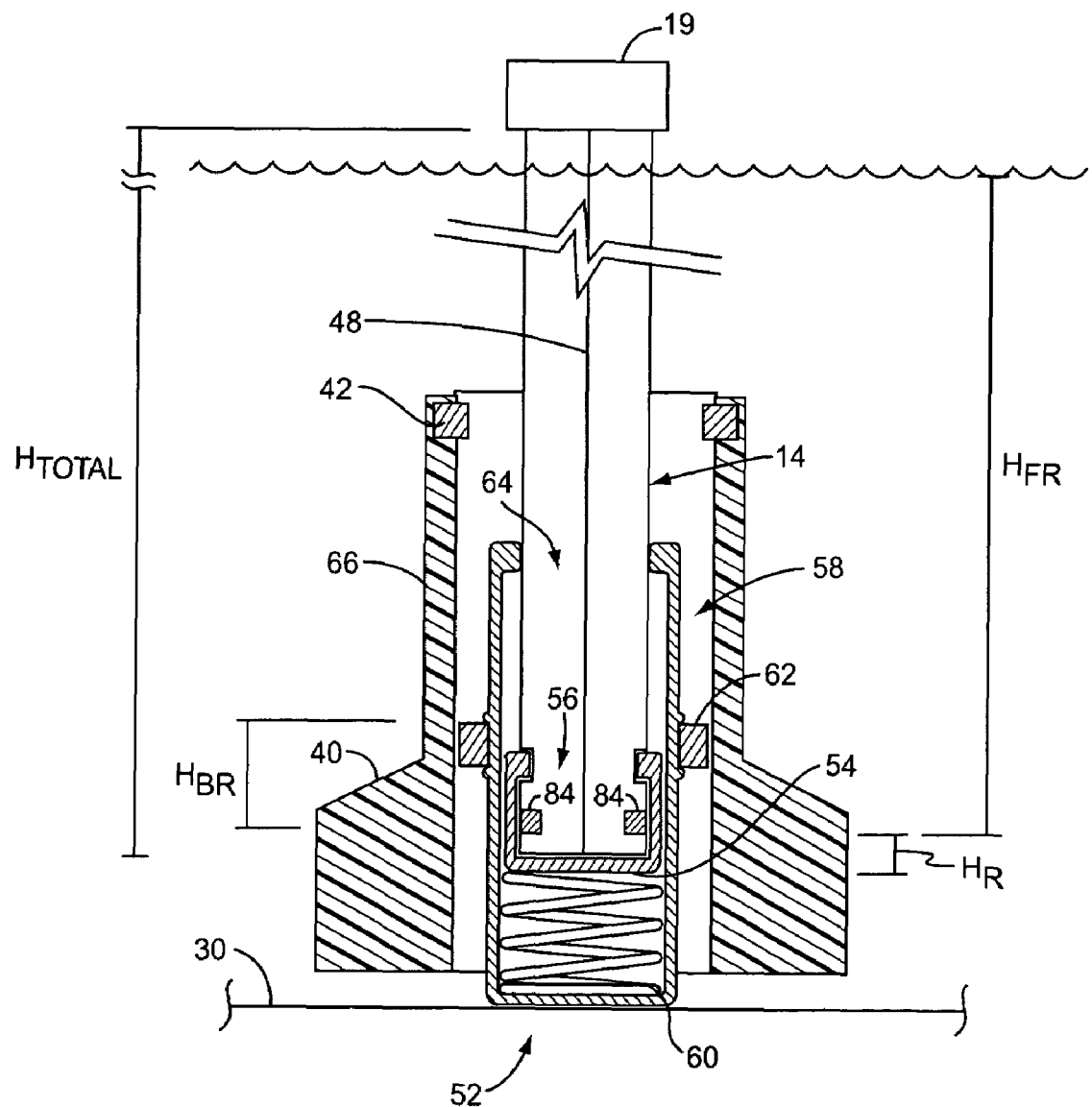
FIG. 6 illustrates a second embodiment of the probe of the present invention.

FIG. 6 illustrates an alternate embodiment of the present invention that improves accuracy of the measurement by eliminating potential non-linearities in the measurements made by the probe 50 as better explained below, although it is more expensive to manufacture than the previous embodiments. Specifically, the embodiment of FIG. 6 adds a probe reference magnet 84 to the probe shaft 14, preferably near the terminal end 56. The probe reference magnet 84 introduces a torsional wave in the magnetostrictive wire 48 just as the other magnets 42, 46, and 62 do. Importantly, the probe reference magnet 84 creates an additional reference point against which the torsional waves from the other magnets 42, 46, and 62 may be compared rather than relying on just the receipt time of the torsional waves.

It has been noted that torsional wave velocity non-linearities may affect the distance measured by the movement of the torsional waves. Specifically, temperature variations may accelerate or slow the torsional wave over the length of the magnetostrictive wire 48. Other similar non-linearities may also be present over the length of the magnetostrictive wire 48. However, most of the non-linearities are relatively time-insensitive such that for a given measurement, all the torsional waves are subjected to the same non-linearities. The probe reference magnet 84 allows the torsional waves to be compared to a fixed reference point (namely, near the end of the magnetostrictive wire 48) rather than simply measured by the sensor in the canister 16. That is, the torsional wave from the reference magnet 62 may be compared to the torsional wave from the probe reference magnet 84. Since the distance along the magnetostrictive wire 48 to the probe reference magnet 84 is known, the sensor may calculate a compensation factor for the non-linearities and apply the same compensation factor to the measurement for the torsional wave from the reference magnet 62. Alternatively, rather than measure the total time of travel for the torsional wave, merely the time difference between the arrivals may be measured to calculate the distance between magnets.

As noted above, the addition of the probe reference magnet 84 adds complexity to the probe 50. Additionally, the magnets 42, 62, and 84 must be spaced far enough apart to differentiate therebetween. As noted above, it has been empirically determined that approximately one inch (2.54 cm) is required so that the torsional waves do not merge and can be differentiated from one another. While shown positioned inside the probe shaft 14, the probe reference magnet 84 could be fixed outside of the probe shaft 14 or fixed to the inner cup 54.

The calculations to derive the fuel density for this embodiment are slightly more complicated than those presented above and are presented below.

As indicated above $H_{TOTAL}$ is the length of the probe shaft 14. In the exemplary embodiment, this is approximately equivalent to the distance ($H_{PRM}$) between the canister 16 and the probe reference magnet 84. If the probe reference magnet 84 was not positioned at the terminal end of the probe shaft 14, then $H_{PRM} < H_{TOTAL}$, but is still a known value. The probe reference magnet 84 is also some distance ($H_R$) above the bottom of probe 54. As illustrated, the probe reference magnet 84 is positioned somewhere above the bottom of the probe 54, and thus $H_R = H_{TOTAL} - H_{PRM}$. $H_R$ is known at the time of manufacturing.

Two variables are measurable with the embodiment of FIG. 6. The first variable is $H_{BR}$, which is equal to the height (vertical distance) between the reference magnet 62 and the probe reference magnet 84. The second variable is $H_{FR}$, which is equal to the height (vertical distance) between the air-fuel interface 36 (as measured by the fuel float magnet 46) and the probe reference magnet 84. Solving for $D_f$ now results in the following equation:

$$D_f = \frac{W_p - K_s(H_{BR} + H_{s0} + H_R - H_1)}{A_p(H_{FR} - H_R)}$$

It is possible that this equation may be restated, but such restatements are considered within the scope of the present invention.

Figure 7:
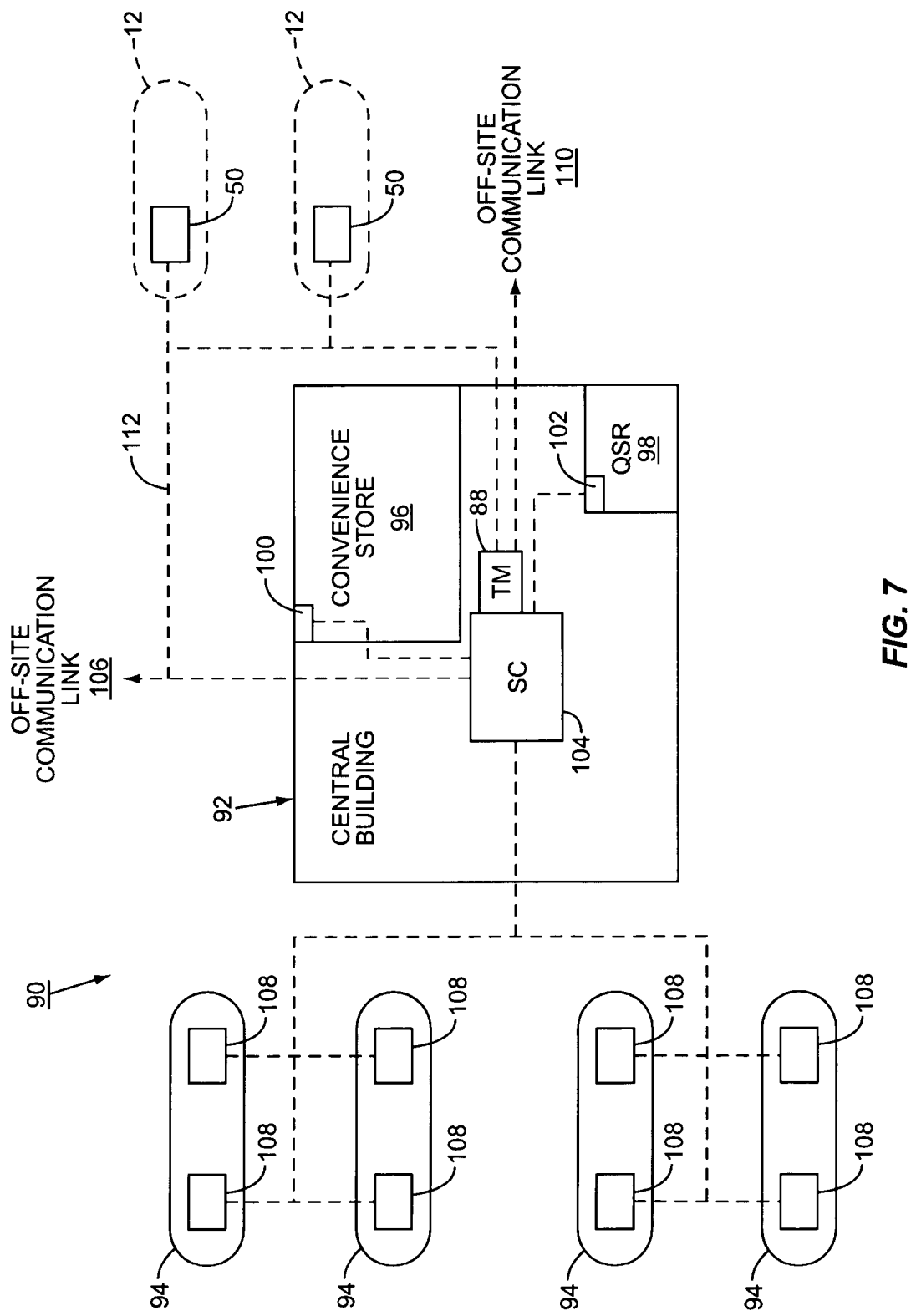
FIG. 7 illustrates a fueling environment incorporating the probe of the present invention.

FIG. 7 illustrates a fueling environment 90 that may incorporate the present invention, and includes the systems and devices that calculate and/or communicate the density of the fuel in the fuel storage tank 12 for the aforementioned purposes. Specifically, the fueling environment 90 may comprise a central building 92 and a plurality of fueling islands 94.

The central building 92 need not be centrally located within the fueling environment 90, but rather is the focus of the fueling environment 90, and may house a convenience store 96 and/or a quick serve restaurant 98 therein. Both the convenience store 96 and the quick serve restaurant 98 may include a point of sale 100, 102 respectively. The central building 92 may further house a site controller (SC) 104, which in an exemplary embodiment may be the G-SITE® POS sold by Gilbarco Inc. of 7300 W. Friendly Avenue, Greensboro, N.C. 27410. The site controller 104 may control the authorization of fueling transactions and other conventional activities as is well understood. The site controller 104 may be incorporated into a point of sale, such as the point of sale 100, if needed or desired. Further, the site controller 104 may have an off-site communication link 106 allowing communication with a remote location for credit/debit card authorization, content provision, reporting purposes, or the like, as needed or desired. The off-site communication link 106 may be routed through the Public Switched Telephone Network (PSTN), the Internet, both, or the like, as needed or desired.

The plurality of fueling islands 94 may have one or more fuel dispensers 108 positioned thereon. The fuel dispensers 108 may be, for example, the ECLIPSE® dispenser or the ENCORE® dispenser sold by Gilbarco Inc. The fuel dispensers 108 are in electronic communication with the site controller 104 through a LAN or the like.

The fueling environment 90 has one or more fuel storage tanks 12 adapted to hold fuel therein. In a typical installation, fuel storage tanks 12 are positioned underground, and may also be referred to as underground storage tanks. Further, each fuel storage tank 12 has a liquid level probe, such as probe 50. The probes 50 report to the tank monitor (TM) 88 associated therewith. Reporting to the tank monitor 88 may be done through a wire-based system, such as an Ethernet LAN, or a wireless system conforming to IEEE standard 802.11g or the like, as needed or desired. The tank monitor 88 may communicate with the fuel dispensers 108 (either through the site controller 104 or directly, as needed or desired) to determine amounts of fuel dispensed, and compare fuel dispensed to current levels of fuel within the fuel storage tanks 12, as needed or desired. In a typical installation, the tank monitor 88 is also positioned in the central building 92, and may be proximate the site controller 104.

The tank monitor 88 may communicate with the site controller 104, and further may have an off-site communication link 110 for leak detection reporting, inventory reporting, or the like. Much like the off-site communication link 106, the off-site communication link 110 may be through the PSTN, the Internet, both, or the like. If the off-site communication link 110 is present, the off-site communication link 106 need not be present, although both links may be present if needed or desired. As used herein, the tank monitor 88 and the site controller 104 are site communicators to the extent that they allow off-site communication and report site data to a remote location.

The present invention capitalizes on the off-site communication link 110 by forwarding data from the probe 50 to the remote location. This data should preferably be protected from tampering such that the site operator cannot alter the data sent to the remote location through either of the off-site communication links 106 or 110. This tamper proof flow of data is provided so that the site operator, who presumably is the one who might be inclined to adulterate the fuel, does not have access to the data that reports on whether the fuel has been adulterated. The data from the probes 50 may be provided to a corporate entity from whom the site operator has a franchise, a governmental monitoring agency, an independent monitoring agency, or the like, as needed or desired. One way to prevent tampering is through an encryption algorithm.

An alternate technique that helps reduce the likelihood of tampering is the use of a dedicated off-site communication link 112, wherein the probes 50 report directly to a location removed from the fueling environment 90. In this manner, the operator of the fueling environment 90 does have not have ready access to the dedicated off-site communication link 112.

For further information on how elements of a fueling environment 90 may interact, reference is made to U.S. Pat. No. 5,956,259, which is hereby incorporated by reference in its entirety. Information about fuel dispensers 108 may be found in U.S. Pat. Nos. 5,734,851 and 6,052,629, which are hereby incorporated by reference in their entireties. For more information about tank monitors 88 and their operation, reference is made to U.S. Pat. Nos. 5,423,457; 5,400,253; 5,319,545; and 4,977,528, which are hereby incorporated by reference in their entireties.

Those skilled in the art will recognize improvements and modifications to the preferred embodiments of the present invention. All such improvements and modifications are considered within the scope of the concepts disclosed herein and the claims that follow.

What is claimed is:

1. A fuel level probe, comprising:
a probe shaft adapted to be positioned in a fuel tank, said probe shaft being buoyant in fuel; and
a spring-loaded foot positioned on a terminal end of the probe shaft to remain fixed with respect to a bottom of said fuel tank as the probe shaft moves due to its buoyancy.

2. The fuel level probe of claim 1, wherein the spring-loaded foot comprises a reference magnet whose height relative to a bottom of the fuel tank is fixed.

3. The fuel level probe of claim 2, further comprising a magnetostrictive wire positioned in the probe shaft, and wherein the magnetostrictive wire generates a reflection based on the reference magnet such that a time measurement of the reflection may be used to determine a length of the magnetostrictive wire positioned above the reference magnet.

4. The fuel level probe of claim 1, wherein the fuel level probe is adapted to measure values from which fuel density can be derived.

5. The fuel level probe of claim 4, further comprising a fuel level float adapted to float at a top surface of fuel within the fuel tank and provide an indication of a fuel level within the fuel tank for the fuel level probe.

6. The fuel level probe of claim 5, further comprising a water level float adapted to float at a level proximate a water-fuel interface within the fuel tank and further adapted to provide an indication of a water level within the fuel tank for the fuel level probe.

7. The fuel level probe of claim 4, wherein the fuel level probe is adapted to report data about values from which the fuel density can be derived to a remote location.

8. A fuel level probe, comprising:
a probe shaft adapted to be positioned in a fuel tank; and
a spring-loaded foot positioned on a terminal end of the probe shaft;
wherein the spring-loaded foot comprises an inner cup and an outer cup.

9. The fuel level probe of claim 8, wherein the spring-loaded foot further comprises a spring positioned between the inner and outer cups.

10. The fuel level probe of claim 9, wherein the inner cup fits on the probe shaft and the probe shaft moves up and down within the outer cup.

11. The fuel level probe of claim 10, further comprising a probe reference magnet associated with the probe shaft and fixedly positioned relative to the probe shaft.

12. The fuel level probe of claim 9, wherein the inner cup and the outer cup delimit respective indentations and the spring is positioned at least partially within the respective indentations to restrict lateral movement of the spring.

13. A fuel level probe, comprising:
a probe shaft adapted to be positioned in a fuel tank; and
a spring-loaded foot positioned on a terminal end of the probe shaft;
wherein the probe shaft comprises a magnetostrictive wire positioned within the probe shaft;
wherein the fuel level probe generates a current on the magnetostrictive wire and detects torsional wave reflections in the magnetostrictive wire; and
wherein the spring-loaded foot comprises a reference magnet and the probe shaft moves relative to the reference magnet such that fuel density can be derived by measuring how much of the probe shaft is positioned above the reference magnet.

14. A system of measuring fuel density in a fuel storage tank, comprising:
a magnetostrictive fuel level probe adapted to determine a fuel level within the fuel storage tank, said magnetostrictive fuel level probe comprising a probe shaft adapted to extend into the fuel storage tank, the probe shaft having a weight ($W_p$);
a foot attached to the probe shaft, the foot comprising:
an outer cup adapted to receive a portion of the probe shaft and allowing the probe shaft to move up and down within the outer cup;
a reference magnet with respect to which the probe shaft moves up and down; and
a spring positioned inside the outer cup and on which the weight rests such that the spring is compressed; and
a control system adapted to determine the fuel density from measurements made by the magnetostrictive fuel level probe regarding a position of the probe shaft relative the reference magnet and the fuel level within the fuel storage tank.

15. The system of claim 14, wherein the foot further comprises an inner cup, wherein the spring is positioned between the inner cup and the outer cup.

16. The system of claim 15, wherein the inner cup and the outer cup both define respective indentations in which the spring rests such that lateral movement of the spring is restricted.

17. The system of claim 15, wherein the probe shaft further comprises a probe reference magnet and the control system knows a distance value for the probe reference magnet.

18. The system of claim 17, wherein the control system calculates the fuel density ($D_f$) according to the following equation:

$$D_f = \frac{W_p - K_s(H_{BR} + H_{s0} + H_R - H_1)}{A_p(H_{FR} - H_R)},$$

wherein $W_p$ is a weight of the magnetostrictive fuel probe,
$K_s$ is a spring constant associated with the spring,
$H_{s0}$ is an unloaded height of the spring,
$H_{BR}$ is equal to the distance between the reference magnet and the probe reference magnet,
$H_R$ is a distance between the probe reference magnet and a bottom of the probe shaft,
$H_1$ is a height of the reference magnet,
$A_p$ is a cross sectional area of the probe shaft, and
$H_{FR}$ is a distance between a height of fuel within the fuel storage tank and the probe reference magnet.

19. The system of claim 17, wherein torsional wave reflections generated by the reference magnet are compared to torsional wave reflections generated by the probe reference magnet.

20. The system of claim 15, wherein the control system calculates the fuel density according to the following equation:

$$D_f = \frac{W_p - K_s(H_{s0} - H_s)}{A_p(H_f - H_s)},$$

wherein $W_p$ is a weight of the magnetostrictive fuel probe,
$K_s$ is a spring constant associated with the spring,
$H_{s0}$ is an unloaded height of the spring,
$H_s$ is a loaded height of the spring,
$A_p$ is a cross sectional area of the probe shaft, and
$H_f$ is a height of fuel within the fuel storage tank.

21. The system of claim 20, wherein the magnetostrictive fuel level probe is adapted to determine the fuel level within the fuel storage tank with a fuel level float and is further adapted to determine a water level within the fuel storage tank with a water level float.

22. The system of claim 14, wherein the control system is adapted to report the fuel density to an off-site location.

23. The system of claim 22, wherein the control system is adapted to report the fuel density to the off-site location directly.

24. The system of claim 22, wherein the control system is adapted to report the fuel density to the off-site location indirectly through a site communicator.

25. The system of claim 22, wherein the control system is adapted to report the fuel density to the off-site location in an encrypted format.

26. The system of claim 14, further comprising a tank monitor and said control system is associated with the tank monitor.

* * * * *